US005849352A

United States Patent [19]
Datta et al.

[11] Patent Number: 5,849,352
[45] Date of Patent: Dec. 15, 1998

[54] SEED STORAGE PROTEIN WITH NUTRITIONALLY BALANCED AMINO ACID COMPOSITION

[76] Inventors: Asis Datta, 104 Uttarakhund Jawaharlal Nevru University New Campus, New Delhi, India, 110067; Anjana Raina, C/O Mr. N. L. Raina A 10 Yojna Vihar, New Delhi, India, 110092

[21] Appl. No.: 635,677

[22] Filed: Apr. 22, 1996

Related U.S. Application Data

[62] Division of Ser. No. 158,270, Nov. 29, 1993.

[51] Int. Cl.$^6$ ............................. A23J 1/00; C07K 1/00; A61K 35/78
[52] U.S. Cl. ......................... 426/656; 530/362; 530/350; 530/370; 530/372
[58] Field of Search ....................... 426/656; 424/195.1; 530/350, 370, 379, 386, 362; 435/6, 7.6, 69.1, 183

[56] References Cited

PUBLICATIONS

Larkins, Genetic Engineering of Plants: An Agricultural Perspective, Genetic Engineering of Seed Storage Proteins (Plenum, NY), pp. 93–118 (1983).
Hoffman et al., Plant Mol. Biol., viol. 11, "A Modified Storage Protein is Synthesized, Processed, and Degraded in the Seeds of Transgenic Plants," pp. 717–729 (1988).
Guerche et al, Mol. Gen. Genet., vol. 221, "Expression of the 2S albumin from Bertholletia excelsa in Brassica napus," pp. 306–314 (1990).
Davies et al, The Biochemistry of Plants, A Comprehensive Treatise, vol. 1, The Plant Cell, Chapter 11, Ribosomes (Academic Press, New York) (1980).
Marchuk, Nucleic Acid Research, vol. 19, No. 5, "Construction of T–Vectors, A Rapid and General System for Direct Cloning of Unmodified PCR Products," p. 1154 (1991).
Paredes–López et al, Lebensm. Wiss. U–Technol., vol. 21, No. 1, Isolation of Amaranth Proteins, pp. 59–61 (1988).
Maniatis et al, Molecular Cloning, A Laboratory Manual, Enzymes Used in Molecular Cloning, Restriction Enzymes, Cold Spring Harbor Laboratory, NY, pp. 104–106 (1982).
Ammerer, Methods in Enzymology, vol. 101, Recombinant DNA, Part C, "Expression of Genes in Yeast Using the ADCI Promoter," pp. 192–201 (1983).
Takaiwa et al, Plant Mol. Biol., vol. 16, "Analysis of the 5' Flanking Region Responsible for the Endosperm–Specific Expression of a Rice Glutelin Chimeric Gene in Transgenic Tobacco," pp. 49–58 (1991).
Broach et al, Experimental Manipulation of Gene Expression, Chapter 5, "Vectors for High Level, Inducible Expression of Cloned Genes in Yeast," pp. 83–117 (1983).
DeGreve et al, J. Mol. Appl Genet., vol. 1, No. 6, "Nucleotide Sequence and Transcript Map of the Agrobacterium tumefaciens Ti Plasmid–Encoded Octopine Synthase Gene," pp. 499–511 (1982).

Rosahl et al, Mol. Gen. Genet., vol. 203, "Isolation and Characterization of a Gene from Solanum tuberosum Encoding Patatin, the Major Storage Protein of Potato Tubers," pp. 214–220 (1986).
Smith et al, Science, vol. 229, "Heterologous Protein Secretion from Yeast," pp. 1219–1229 (1985).
Horsch et al, Science, vol. 227, "A Simple and General Method for Transferring Genes into Plants," pp. 1229–1231 (1985).
Prestidge et al, Anal. Biochem., vol. 97, "Preparative Flatbed Electrofocusing in Granulated Gels with Natural pH Gradients Generated from Simple Buffers," pp. 95–102 (1979).
Laemmli, Nature, vol. 227, "Cleavage of Structural Proteins During the Assembly of the Head of Bacteriophage T4," pp. 680–685 (1970).
O'Farrell, J. Biol. Chem., vol. 250, No. 10, "High Resolution Two–Dimensional Electrophoresis of Proteins," pp. 4007–4021 (1975).
Elledge et al, Mol. Cell. Biol., vol. 7, No. 8, "Identification and Isolation of the Gene Encoding the Small Sub–unit of Ribonucleotide Reductase from Saccharomyces cerevisiae: DNA Damage–Inducible Gene Required for Mitotic Viability," pp. 2783–2793 (1987).
Towbin et al, Proc. Natl. Acad. Sci. USA, vol. 76, "Electrophoretic Transfer of Proteins from Polyacrylamide Gels to Nitrocellulose Sheets: Procedure and Some Applications," pp. 4350–4354 (1979).
Ausubol et al, Current Protocols in Molecular Biology, Phenol/SDS Method for Plant RNA Preparation (Greene Publishing Associates and Wiley–Interscience, New York, pp. 4.3.1–4.3.3 (1987).
Okayama et al, Methods in Enzymology, vol. 154, Construction and Screening of cDNA Libraries, "High–Efficiency Cloning of Full–Length cDNA; Construction and Screening of cDNA Expression Libraries for Mammalian Cells," pp. 3–28 (1987).
Anderson et al, Methods in Enzymology, vol. 96, "Immuno–precipitation of Proteins from Cell–Free Translations," pp. 111–120 (1983).
Ricciardi et al, Proc. Natl. Acad. Sci. USA, vol. 76, No. 10, "Purification and Mapping of Specific mRNAs by Hybridization–Selection and Cell–Free Translation," pp. 4927–4931 (1979).

(List continued on next page.)

Primary Examiner—Robert A. Wax
Assistant Examiner—Tekchand Saidha
Attorney, Agent, or Firm—Kerkam, Stowell, Kondracki & Clarke; Dennis P. Clarke

[57] ABSTRACT

The present invention relates, in general to protein that is a seed storage protein having high nutritional value. In particular, the invention relates to the protein AmA1 and to a DNA sequence encoding same. The invention further relates to a recombinant molecule comprising the AmA1 encoding sequence and to a host cell transformed therewith. In addition, the invention relates to a method for producing transgenic plants with high nutritionally rich amino acids.

3 Claims, 9 Drawing Sheets

OTHER PUBLICATIONS

Gubler et al, Gene, vol. 25, "A Simple and Very Efficient Method for Generating cDNA Libraries," pp. 263–269 (1983).

Young et al, Proc. Natl. Acad. Sci. USA, vol. 80, "Efficient Isolation of Genes by Using Antibody Probes," pp. 1194–1198 (1983).

Manfioletti et al, Nucleic Acids Res., vol. 16, No. 7, "A New and Fast Method for Preparing High Quality Lambda DNA Suitable for Sequencing," pp. 2873–2884 (1988).

Chamberlain, Anal. Biochm., vol. 98, "Fluorographic Detection of Radioactivity in Polyacrylamide Gels with the Water–Soluble Fluor, Sodium Salicylate," pp. 132–135 (1979).

Feinberg et al, Anal. Biochem., vol. 137, "A Technique for Radiolabeling DNA Restriction Endonuclease Fragments to High Specific Activity," pp. 266–267 (1984).

Rogers et al, Plant Mol. Biol. Manual D1, "Extraction of Total Cellular DNA from Plants, Algae and Fungi," eds. Gelvin et al, Kluwer Academic Publishers, pp. 1–8 (1994).

Higgins, Annu. Rev. Plant Physiol., vol. 35, "Synthesis and Regulation of Major Proteins in Seeds," pp. 191–221 (1984).

Perlman et al, J. Mol. Biol., vol. 115, "Localization of Genes for Variant Forms of Mitochondrial Proteins on Mitochondrial DNA of *Saccharomyces cerevisiae*," pp. 675–694 (1977).

Von Heijne, J. Mol. Biol., vol. 173, "How Signal Sequences Maintain Cleavage Specificity," pp. 243–251 (1984).

Raina et al, Proc. Natl. Acad. Sci. USA, vol. 89, "Molecular Cloning of a Gene Encoding a Seed–Specific Protein With Nutritionally Balanced Amino Acid Composition from *Amaranthus*," pp. 11774–11778 (1992).

Salinovich et al, Anal. Biochem., vol. 156, "Reversible Staining and Peptide Mapping of Proteins Transferred to Nitrocellulose after Separation by Sodium Dodecylsulfate–Polyacrylamide Gel Electrophoresis," pp. 341–347 (1986).

```
                              M   A   G   L   P
ATCAGATTAACATAATTCACAATAAAAAAAAAAAGAGCTTAAATGGCGGGATTACC      60

V   I   M   C   L   K   S   N   N   N   Q   K   Y   L   R   Y   Q   S   D   N
AGTGATTATGTGCCTAAAATCAAATAACAACCAGAAGTACTTAAGATATCAAAGTGATAA  120

I   Q   Q   Y   G   L   L   Q   F   S   A   D   K   I   L   D   P   L   A   Q
TATTCAACAATATGGTCTTCTTCAATTTCAGCTGATAAGATTTTAGATCCATTAGCTCA   180

F   E   P   S   K   T   Y   D   G   L   V   H   I   K   S   R   Y   T
ATTTGAAGTCGAACCTTCCAAGACTTATGATGGTCTTGTTCACATCAAATCTCGCTACAC  240

N   K   Y   L   V   R   W   S   P   N   H   Y   W   I   T   A   S   A   N   E
TAACAAATATTTGGTTAGGTGGTCTCCCAATCATTATTGGATTACAGCAGCCAATGA    300

P   D   E   N̄   K   S   N   W   A   C   T   L   F   K   P   L   Y   V   E   E
ACCAGATGAAAATAAAAGCAATTGGGCATGCACATTATTCAAACCACTTTACGTAGAAGA  360

G   N   M   K   K   V   R   L   L   H   V   Q   L   G   H   Y   T   E   N̄   Y
AGGTAACATGAAAAAGGTTCGACTTTTGCACGTCCAATTAGGTCATTATACAGAAAATTA  420

T   V   G   G   S   F   V   S   Y   L   F   A   E   S   S   Q   I   D   T   G
TACCGTTGGTGGGTCCTTCGTATCATACTTATTGCCGAATCAAGTCAAATTGATACCGG   480

S   K   D   V   F   H   V   I   D   W   K   S   I   F   Q   F   P   K   T   Y
CTCTAAAGACGTATTCCATGTCATAGATTGGAAATCAATCTTTCAATTTCCCAAAACATA  540
```

FIG. 9B

```
  V  T  F  K  G  N  N  G  K  Y  L  G  V  I  T  I  N  Q  L  P
TGTCACATTTAAAGGAAATAATGGAAAATATTTAGGGGTTATCACATTAATCAACTTCC      600

C  L  Q  F  G  Y  D  N  L  N  D  P  K  V  A  H  Q  M  F  V
ATGTCTACAATTTGGGTATGATAATCTTAATGATCCAAAGGTGGCTCATCAAATGTTTGT     660

T  S  N̄  G  T  I  C  I  K  S  N  Y  M  N  K  F  W  R  L  S
CACTTCTAATGGTACTATTTGCATTAAATCCAATTATATGAACAAGTTTTGGAGACTCTC     720

T  D  N  W  I  L  V  D  G  N  D  P  R  E  T  N  E  A  A  A
TACGGATAATTGGATATTAGTCGATGGGAATGATCCTCGCGAAACTAATGAAGCTGCTGC     780

L  F  R  S  D  V  H  D  F  N  V  I  S  L  L  N  M  Q  K  T
GTTGTTTAGGTCGGATGTGCATGATTTTAATGTGATTTCGCTTTTGAACATGCAAAAAAC    840

W  F  I  K  R  F  T  S  G  K  P  E  F  I  N  C  M  N  A  A
TTGGTTTATTAAGAGATTTACGAGTGGTAAGCCTGAGTTTATAAATTGTATGAATGCAGC    900

T  Q  I  V  D  E  T  A  I  L  E  I  I  E  L  G  S  N  N
TACTCAAATTGTTGATGAAACTGCTATTTTAGAGATAATAGAATTGGATCCAACAACTA     960

ATATATTGGATTGCTTTAAGATTCAAATTAAAGTCTAGTTGTTAATGTAAGGAATAAAA    1020

CGTTGTAAGTCGTCTCTTTGGAAACAAGAGGGTTCTTCCTTGTATCATATCTCTATGGTC   1080

TCTTTCAGATTTTGACCATAAGATTACTATTAAATACTTGTAAATGTGTTTGTCTGTGATG  1140

ATTACTCTTTGTTGGAATAAATAATTGTTAGAATTATATTAC                    1183
```

SEED STORAGE PROTEIN WITH NUTRITIONALLY BALANCED AMINO ACID COMPOSITION

This is a division of application Ser. No. 08/158,270 filed Nov. 29, 1993.

BACKGROUND OF THE INVENTION

1. Technical Field

The present invention relates, in general, to a seed storage protein from Amaranthus hypochondriacus with nutritionally balanced amino acid composition. In particular, the invention relates to the AmA1 (Amaranth Albumin 1) protein and to a DNA sequence encoding same. The invention further relates to a recombinant molecule comprising AmA1 encoding sequence and to a host cell transformed therewith. In addition, the invention relates to a method for improving the nutritional quality of some crop plants.

2. Background Information

Seed storage proteins, intended as a source of nitrogen for germinating seedlings, form an important source of dietary protein for human beings. A balanced composition of amino acids is therefore required in the human diet, but most often seeds a deficient in one or the other essential amino acids. For years plant breeders have tried to improve the balance of essential amino acids of the important crop plants (Larkins, B. A. (1983) in Genetic Engineering of Plants: An Agricultural Perspective (Plenium, New York), pp. 93–118). Molecular approaches for improving the nutritional equality of seed proteins provide alternatives to the conventional approaches. Attempts in vitro mutagenesis of the coding region of certain seed proteins has been tried to increase the levels of essential amino acids (Larkins, supra and Hoffman, L. M., Donaldson, D. D. & Herman, E. M. (1988) Plant Mol. Biol. 11, 717–729). Another approach is to transfer heterologous storage protein genes that encode proteins with higher levels of limiting amino acids (Guerche, P., De Almeida, E., Schwarztein, M. A., Gander, E., Krebbers, E. & Pelletier, G. (1990) Mol. Gen. Genet. 221, 306–314). Expressing high levels of a particular amino acid by heterologous gene transfer or by mutation may be detrimental to the normal physiology of seed development. This may also produce seeds with a biased amino acid composition. An alternative approach will therefore be to express a gene for a heterologous protein with a balanced amino, acid composition.

Grain Amaranth is a pseudo cereal with high protein content (17–19% of seed dry weight) as compared to more traditional crops which have an average of about 10% protein (Davies et al. (1980) in The Biochemistry of Plants (Academic Press, New York)). Its protein is rich in essential amino acids like lysine, tryptophan and sulphur amino acids (Senft, J. P. (1980) in Proceedings of the 2nd Amaranth conference (Rodale Press, Pennsylvania), pp. 43–47), that are otherwise deficient in the major seed proteins of legumes and cereals. It can therefore be used as a source of a gene that encodes a protein of high nutritional value. In spite of good quality and quantity, these proteins have not yet been purified and characterized. In Amaranthus, 50% of the total seed proteins at maturity are globulin and albumin (Paredes-Lopez, O., Mora-Escobedo, R. & Ordorica-Falonir, C. (1988) Lebensm. Wiss U-Technol. 21, 59–61). The present invention provides purified AmA1 (Albumin seed storage protein) and a DNA sequence encoding same. The invention also provides a step toward developing transgenic plants with a balanced amino acid composition.

OBJECTS OF THE INVENTION

An object of the invention is to propose a protein that is a seed storage protein having nutritional value.

Another object of this invention is to isolate, characterize and construct a gene that can be used in the expression of albumin seed storage protein in plants.

A further object of this invention is to propose a recombinant molecule comprising the AmA1 encoding sequence and to a host cell transformed therewith.

It is a further object of this invention to introduce AmA1 gene into plants such as field crops such as rice, maize, wheat and legumes, vegetables crops such as carrot, potato etc. thereby improving the nutritional quality of such plants.

BRIEF DESCRIPTION OF INVENTION

The present invention is broadly directed to the use of a seed storage protein, as exemplified by AmA1, for commercial uses such as in the brewing industry or for agronomic uses such as to improve human dietary protein by introducing the gene into major cereal and legumes.

The present invention also relates to AmA1 substantially purified and characterized. The AmA1 is an albumin protein with a pH value of 6.8. The protein is a 35 kDa, monomer with four isoforms that can be separated by chromatofocussing. AmA1 is a cytosolic protein. Unlike to any other seed storage proteins neither is it localized in protein bodies nor does it have any glycosylation.

The present invention also relates to substantially all of a substantially pure gene encoding a seed storage protein AmA1 with a specific DNA sequence as shown in SEQ ID NO:1. The gene encodes an albumin protein exhibiting high nutritional quality having a molecular weight of 35 kDa, as determined by SDS-PAGE.

The invention relates to compositions for use in raising transgenic plants, which compositions have balanced amino acid, in particular AmA1 protein expression. Specifically, the protein has a high proportion of essential amino acids such as lysine, leucine, threonine, phenylalanine, valine and sulfur amino acids that are otherwise deficient in major seed proteins of legumes and cereals. The AmA1 amino acid composition is comparable to the World Health Organization (WHO) recommended values for a highly nutritional protein, making it more important nutritionally. An agronomic use for such a protein is to combine the compounds with an appropriate carrier, which is agronomically acceptable, permitting delivery of the compound directly to the plant or to the soil in which the plants grow.

A transformed plant cell is also disclosed Herein, which cell is transformed with a gene encoding AmA1 protein. The gene encoding such a protein can include the DNA sequence set forth in SEQ ID NO:1.

Further objects and advantages of the present invention will be clear from the description of the invention that follows:

BRIEF DESCRIPTION OF THE DRAWINGS

FIGS. 1A–1D Purification of 35 kDa protein.

FIGS. 3A and 3B Analysis of subclones.

FIGS. 4A–4D Expression of AmA1 gene during seed development. (FIGS. 4A and 4B) Crude extract (20 μg of Protein) of seeds at various stages of development, as in Table I, were resolved by SDS/PAGE on a 12% gel in duplicate. Protein bands in one gel were stained with Coomassie Blue (FIG. 4A) and in the other were subjected to Western blot analysis (FIG. 4B). (FIG. 4C and 4D) Total RNA was extracted from developing seeds and 2-μg sample were separated on a 1.2% agarose gel containing glyoxal in duplicate. RNA integrity was checked by ethidium bromide staining (FIG. 4C). AmA1-specific mRNA was identified by Northern blot analysis. RNA was transferred to GeneScreen-Plus and probed with labeled AmA1 cDNA (FIG. 4D).

FIGS. 5A and 5B Seed-specific expression of AmA1 gene. Total RNA was isolated from the following tissues. (FIG. 5A) Lanes: 1, seedling; 2, seed; 3, root; 4, leaf. (FIG. 5B) Lanes: 1, leaf; 2, root; 3, seed; 4, 1-day-old seedling. (FIG. 5A) Ethidium bromide-stained gel to show the integrity of rRNA bands. Arrows indicate the rRNA bands. (FIG. 5B) Northern blot probed with labeled AmA1 cDNA.

Figure 1A:
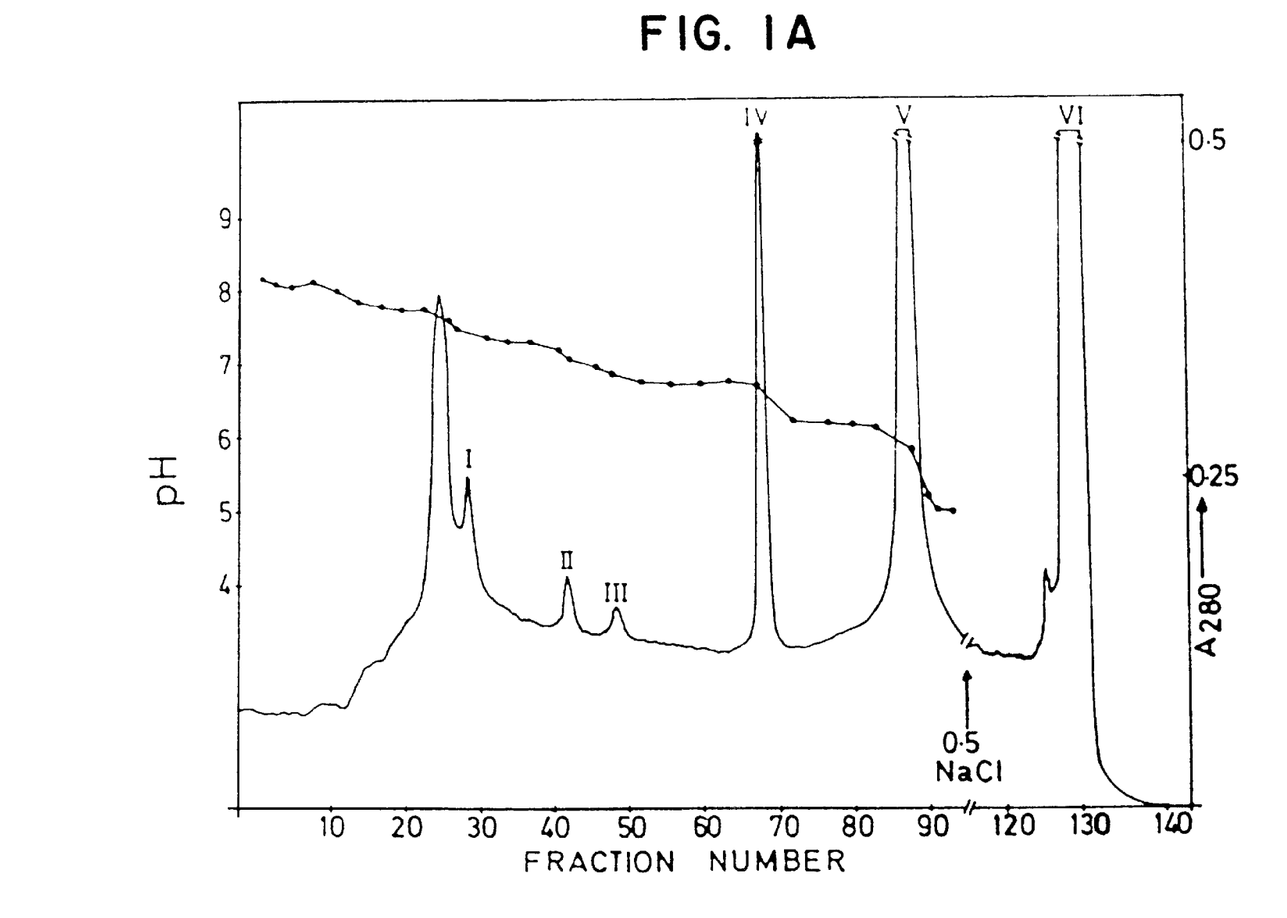
(FIG. 1A) Elution profile of the Chromatofocussing column; , $A_{280}$; pH; I-IV, protein peaks. The unnumbered peak before peak I did not contain protein.
Figure 1B:
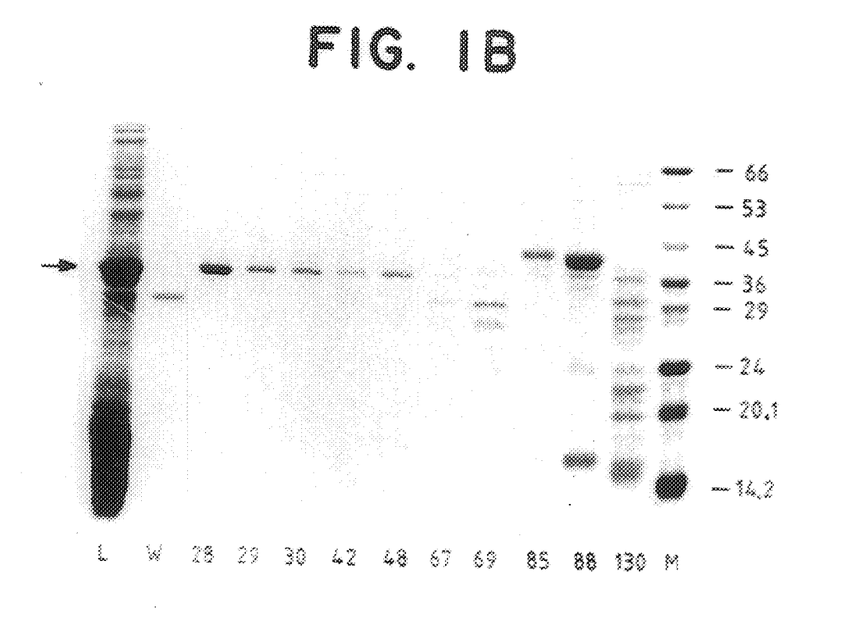
(FIG. 1B) SDS/PAGE analysis column fractions. L, material loaded; W, wash; M, molecular mass standards, Numbers indicate the fractions analyzed. Arrow indicates the 35 kDa protein. Equal volumes of each fraction were analyzed.
Figure 1C:
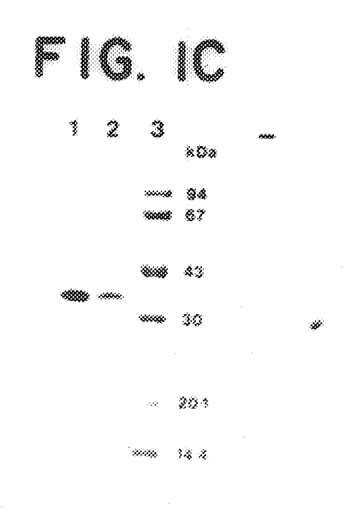
(FIG. 1C) Purity of AmA1 by one-dimensional gel electrophoresis. The purified protein 10 μg (lane 1) and 5 μg (lane 2) of the purified protein was analyzed on 12% SDS/PAGE and stained with Coomassie Blue. Lane 3 shows molecular mass standards.
Figure 1D:
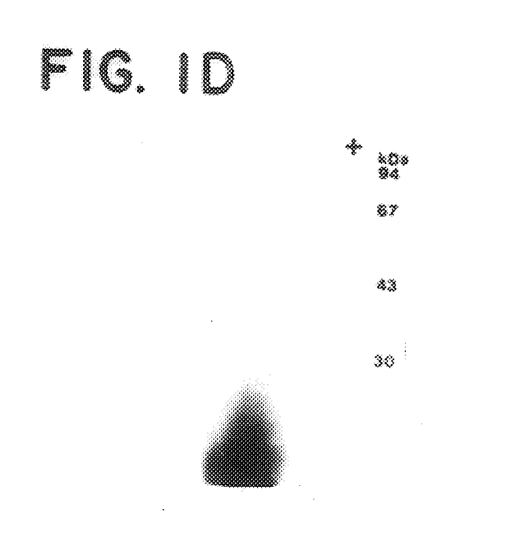
(FIG. 1D) Purity of AmA1 by two-dimensional gel electrophoresis. Protein (5 μg) was analyzed in the first dimension by SDS/PAGE on a 10% gel and stained with Coomassie Blue. Dark patch at the bottom of the gel contains the ampholytes.
Figure 2:
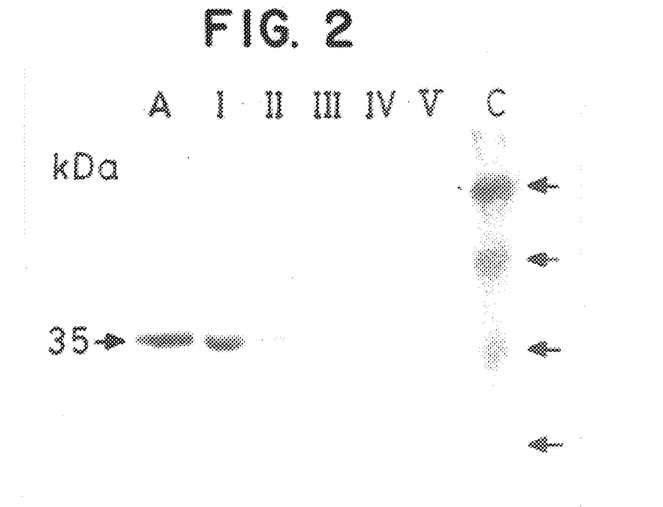
FIG. 2 Western blot analysis of peak fractions from a chromatofocussing column probed with AmA1 antibodies. Equal volumes of sample from fractions obtained after chromatofocussing were resolved by SDS/PAGE on a 12% gel and transferred to nitrocellulose. Immunoreactive polypeptides were detected with AmA1 antibodies. Lanes; A, Albumin fraction and I-V, peak fractions (FIG. 1A) analyzed by SDS/PAGE; C, albumin fraction analyzed on an isoelectric focussing gel prior to immunodetection. Arrows indicate the various isoelectric forms. Fourth band is very faint and thus not very clear.

The purification of AmA1 from *Amaranthus hypoclondriacus* is described in the Examples below, as is the characterization of the isolated protein. The four forms of the protein were resolved on chromatofocussing column at pH 7.4, 7.1, 6.8 and 6.7. Protein eluting at pH 7.4, AmA1 (peak 1) was further purified on a gel filtration column. FIGS. 1A, 1C, and 1D show the purity of the protein by one and two dimensional gel electrophoresis. Antibodies raised against purified peak 1 protein showed immunoreactivity with the 35 kDa polypeptide present in other peaks, indicating that the protein may have at least four isoforms (FIG. 2). Analysis of the albumin fraction on an isoelectric focussing gel visible on immunostaining (FIG. 2, Lane C) further confirms the existence of four isoforms. The protein is a 35 kDa water-soluble, non-glycosylated monomer with four isoforms, having an acidic pH. Analysis of RNA and protein in developing seeds showed that AmA1 is synthesized during early embryogenesis (FIGS. 4A and 4B), reaching a maximum by midmaturation. No RNA was detected in one day old seedlings although the protein showed delayed breakdown on germination, thus indicating its developmental regulation. Mature seeds even after one year of storage contained AmA1 mRNA, although at reduced levels suggesting that it is very stable.

The gene encoding the plant derived AmA1 protein having the sequence shown in SEQ ID NO:1: was cloned as described in the Examples that follow. Briefly, the cDNA encoding the protein was obtained by immunoscreening a lambda gt11 expression library. In vitro translation of hybrid-selected mRNA gave a 35 kDa protein. Genomic Southern hybridization indicated that AmA1 is encoded by a single gene. Affinity purified AmA1 antibodies were used to isolate cDNA clones from developing-seed expression library. The six immunopositive plaques recombinant obtained were found to be related. The cDNA of the largest clone (1.2 kb) has a single major open reading frame corresponding to a 304-amino acid polypeptide. The clone was confirmed by hybrid-selected translation and immunoprecipitation.

The gene having the structure of SEQ ID NO: 1: containing the coding sequence for the mature AmA1 protein can be attached to genetic regulatory elements that are needed for the expression of the structural gene in a defined host cell. The first type of regulatory element required is a gene promoter region, which contains DNA sequences recognized by the biological machinery of the plant cell and which induces transcription of the DNA sequence into messenger RNA (mRNA). The mRNA is then translated into the protein product coded for by the structural gene region. The promoter is attached in front of or 5' to the gene for AmA1, which can be performed according to standard methods known in the art. See, for example, Maniatis et al, (1982) Molecular Cloning, Cold Spring Harbor Laboratory, New York, pp. 104–106.

Promoter regions which can be used for expression of the AmA1 gene in plant cells include promoters which are active in a wide range of different plant tissues. For example, the 35S promoter from the cauliflower mosaic virus may be suitable for this purpose. Another type of promoter that can be used in plant cells is one that expresses under more restricted conditions. Included in this class are promoters active only in certain tissue(s) of the plant and/or induced to be active by certain stimuli like wounding. An example of this kind of promoter is the 5' regulatory region from the gene for gluteline, patatin, RUBPcase. These types of promoters are discussed in (Takaiwa et al., Plant Mol. Biol. 16, 49–58, 1991). Expression of the AmA1 gene in yeast hosts can be achieved by use of promoters obtained from yeast sources. Examples of such promoters include the gal, adh promoter for expression in yeast such as YEP51, pAAH5 as exemplified in Gustav Ammerer, In methods in Enzymology, vol.101, pp. 192–201 & Branch et al., Experimental Manipulation of gene expression, pp.83–117. The gene promoter sequences can also be derived in part or in whole from promoter sequences found in cells unlike those of the host cells as long as they meet the above criteria for transcription and translation.

A second genetic regulatory element which desirably can be, but need not be, attached to the AmA1 protein gene is a terminator or polyadenylation sequence that promotes effective termination of transcription of the gene and, in eukaryotes, also promotes polyadenylation, i.e., the addition of any number of adenosine nucleotides at the 3' end of the mRNA. Standard methods known in the art can be used to attach the terminator region behind or 3' to the gene. (See, for example, T. Maniatis et al, supra, pp. 104–106). An example of such a terminator/polyadenylation sequence for expression in plants is that from the octopine synthase gene and or nopaline synthase gene from an *Agrobacterium tumefaciens* Ti plasmid as enunciated in DeGreve et al, (1982), J. Mol. Appl. Genet. 1: 499–511. The gene terminator sequences can also be derived in part or in whole from terminator sequences found in cells unlike those of the host cell, as long as they meet the above criteria for transcription termination and polyadenylation required by the host cell.

Another type of regulatory element which can be attached to the gene for AmA1 is a DNA sequence coding for a signal peptide. The signal peptide is attached the amino terminus of the protein and permits the protein to be localized inside the protein bodies or secreted from the host cell. During this localization process, the signal peptide is cleaved off, producing a protein product with the sequence of the mature protein. The DNA sequence for the signal peptide is inserted between the promoter and the coding region. Standard methods known in the art may be used to attach the DNA sequence for the signal peptide (see, for example, Maniatis, T., et al, supra, pp. 104–106). Examples of such signal sequences include the signal peptide from a patatin gene and or gluteline gene of plants (Rosahl et al., Mol. Gen Genet. 203, 214–220, 1986) and from prepro factor of yeast (Smith et al, 1985, Science 229: 1219–1229). The signal peptide sequences can also be derived in whole or in part from signal sequences found in cells unlike those of the host cell, as long as they meet the above criteria for processing and localization of the protein in the host cell.

Any of the various methods known for introducing foreign genes into plants can be used for insertion of AmA1 gene into a host plant. The methodology chosen to accomplish plant transformation with the AmA1 gene varies depending on the host plant. By way of example, one well-characterized methodology that would be useful for plant transformation with AmA1 gene is Agrobacterium mediated transformation.

Agrobacterium mediated transformation using the AmA1 gene follows the procedure well-known for this methodology. First, a gene cassette suitable for expression in plants is introduced into a disarmed strain of *Agrobacterium tumefaciens* as in intermediate host. The AmA1 gene cassette is introduced into the T-DNA region of a recombinant plasmid containing a selectable marker gene such as a gene encoding for neomycin phosphotransferase II, phosphinothricin acetyl transferase, or the like. This methodology is set forth in many literature publications including Horsch et al, (1985), science 227: 1229–1231. Pieces of plant tissue, e.g. leaf, cotyledons or hypocotyl are co-incubated with the bacteria for 2–3 days before the bacteria are killed using antibiotics such as carbenicillin. Additional antibiotics corresponding to the selectable marker gene employed are included in the plant tissue culture medium such that only transformed plant cells will grow.

Plants regenerated from the transformed cells are then tested for the presence and expression of the AmA1 gene. Immunoassays and tests for AmA1 protein activity can be used to identify individual transformants.

As noted, several other methodologies are available for plant transformation apart from Agrobacterium transformation. Examples of these other DNA delivery methods include electrophoration, i.e. chemically induced delivery into protoplasts, micro-injection, biolistics, as well as others. Examples of types of plants that are not especially suitable for Agrobacterium-mediated transformation are legumes and certain cereals including rice. These plants would plainly benefit from plant transformation attempts using biolistic approaches.

Certain aspects of the present invention will be described in greater detail in the non-limiting Examples that follow.

EXAMPLE 1

PURIFICATION AND CHARACTERIZATION OF AMA1 PROTEIN

Experimental Protocols:

Plant material

Seeds of *Amaranthus hypochondriacus* were obtained from National Bureau of Plant Genetic Research, Simla, India. Mature seeds were ground to a fine powder and defatted by extraction with cold acetone. Seeds and the defatted seed meal were stored at 4° C. under desiccation. Seeds at different developmental stages were kept frozen until use.

Purification and Characterization of 35 kDa albumin

Defatted seed meal (1 g) was extracted with 10 ml of buffer A (25 mM Tris acetate, pH 8.5) containing 1M NaCl and 2 mM Phenyl methyl sulfonyl fluoride. Homogenate was centrifuged and the supernatant was dialyzed against buffer A. Precipitate formed on dialysis was removed by centrifugation and the supernatant was chromatographed on a DEAE-Sepharose column (1×25 cm; 25 ml/h), pre-equilibrated with buffer A. Column was washed with the same buffer and the bound protein was eluted with a multicomponent buffer system, as suggested by Prestidge and Hearn (*Anal. Biochem.* 97, 95–102, 1979) with slight modifications. Fractions (2 ml) were collected and analyzed on SDS/PAGE. Appropriate fractions, after analysis on SDS/PAGE, were concentrated using centricon (Amicon) and subjected to further purification on a Sephadex G-75 (1.6×30 cm) column previously equilibrated with buffer A containing 0.1M NaCl. Elution was carried out in the same buffer at a flow rate of 10 ml/h. Fractions were analyzed on SDS/PAGE and pure protein was concentrated and stored at 4° C.

SDS/PAGE and NEPHGE

Purity of the sample was routinely checked by SDS/PAGE using 12% separating and 4% stacking gel according to the procedure of Laemmli (*Nature* 227, 680–685, 1970). The gels were stained with Coomassie Brilliant Blue R-250. Non-equilibrium pH gradient electrophoresis (NEPHGE) was performed by the procedure of O'Farrell et al. (*J. Biol. Chem.* 250, 4007–4021, 1975). Purified protein or crude albumin fraction was separated by NEPHGE in the first dimension using Pharmalyte pH 3–10 (Pharmacia). The gel was equilibrated in SDS sample buffer prior to second dimension gel.

Antisera preparation and immunodetection Antibodies against purified AmA1 were raised in rabbits. They were affinity purified essentially by the procedure of Elledge and Davis (*Mol. Cell. Biol.* 7, 2783–2793, 1987). Western blot analysis was done as described by Towbin et al. (*Proc. Natl. Acad. Sci. USA* 76, 4350–4354, 1979). Protein bands were visualized by staining with Ponceau S (Salinovich, O. & Montelaro, R. (1986) *Anal. Biochem.* 156, 341–347) prior to immunodetection. Antibodies were used at a dilution of 1:10,000 (crude antibodies) or 1:5,000 (affinity-purified antibodies). Alkaline phosphatase conjugated anti-rabbit IgG (Promega) was used as secondary antibody. Amino acid analysis The amino acid content of the purified protein was determined by the LKB Alpha plus 4151 amino acid analyser. Samples were hydrolysed with 6N HCl under vacuum at 105° C. for 22 h prior to analysis.

RNA isolation

Total RNA was isolated by Phenol/Chloroform extraction and LiCl precipitation procedure described by Ausu 1 et al. (*Current Protocols in Molecular Biology*, Greene Publishing Associates and Wiley-Interscience, New York, pp. 4.3.1–4.3.3, 1987). Poly(A)$^+$ RNA was isolated from total RNA by two rounds of selection on oligo (dT) cellulose according to the procedure of Okayama et al. (In *Methods Enzymol.* 154, 3–28, 1987).

in vitro translation and immunoprecipitation

RNA (2 $\mu$g) or Poly(A)$^+$ RNA (0.5 $\mu$g) was translated in a rabbit reticulocyte lysate system (Promesa) and immunoprecipitated according to the procedure of Anderson and Blobel (*Methods Enzymol.* 96, 111–120, 1983) except that antibodies were bound to protein A-Sepharose beads in 0.1M sodium phosphate buffer, pH 8.0 prior to immunoprecipitation. Immunoprecipitated product was boiled in SDS sample buffer and electrophoresed. Gel was stained and fluorography was done (Chamberlain, J. P. (1979) *Anal. Biochem.* 98, 132–135). It was exposed to X-Ray film at −70° C. Hybrid selected translation of AmA1 mRNA was done according to the procedure of Ricciardi et al (*Proc. Natl. Acad. Sci. USA* 76, 4927–4931, 1979).

Results:

Albumin fraction obtained on dialysis of the crude extract was chromatographed on chromatofocussing column. On chromatofocussing, 35 kDa albumin protein eluted in four different peaks at pH values of 7.4, 7.1, 6.8 and 6.7 (a faint band but clearly visible on immunoblotting (FIGS. 1A & 1B); other two peaks did not have any 35 kDa albumin protein. Protein eluting at pH 7.4, AmA1 (peak I), was maximum and was further purified on a gel filtration column (data not shown). FIGS. 1C and 1D show the purity of the protein by one and two dimensional gel electrophoresis. Antibodies raised against purified peak I protein showed immunoreactivity with the 35 kDa polypeptide present in other peaks, indicating that the protein may have at least four isoforms (FIG. 2). When albumin fraction was analyzed on IEF gel, three distinct bands and a fourth faint band were visible on immunostaining (lane C, FIG. 2). It further confirmed the existence of isoforms.

EXAMPLE 2

MOLECULAR CLONING AND EXPRESSION OF DNA ENCODING AMA1 PROTEIN

Experimental Protocols:

cDNA construction and screening

Poly(A$^+$) RNA isolated at the stages when AmA1 mRNA was high (stages III and IV, Table I) was used as a template for cDNA synthesis. cDNA was synthesized by the method of Gubler and Hoffman (*Gene* 25, 263–269, 1983) and cloned in lambda gt11 according to Young and Davis (*Proc. Natl. Acad. Sci. USA* 80, 1194–1198, 1983). Briefly, first strand cDNA synthesis was carried out using reverse transcriptase and oligo (dT) as primer (Amersham cDNA synthesis kit). cDNA was sequentially treated with S1 nuclease, EcoRI methylase and Klenow fragment of DNA polymerase I prior to blunt end ligation to EcoRI linkers. Linkered cDNA was ligated to EcoRI ended lambda gt11 arms (Amersham cDNA cloning kit). Resulting DNA was packaged in vitro and used to infect *E. coli* strain Y1090. About 17000 recombinant phages were plated on two 150 mm plates, induced with IPTG and fusion proteins were detected by immunoscreening using AmA1 antibodies.

Subcloning of insert DNA

Lambda DNA was purified by the CTAB procedure of Manfioletti and Schneider (*Nucleic Acids Res.* 16, 2873–2884, 1988). Insert was purified from the EcoRI digested recombinant lambda DNA and ligated to EcoRI cut pTZ18U and Ml3mp18 vector DNA. *E.coli* strains JM101 and JM109 served as hosts for plasmid and phage vectors respectively. Plasmid and M13 DNA was purified by standard protocols (Sambrook J., Fritsch, E. F. & Maniatis, T. (1989) *Molecular Cloning: A Laboratory Manual* (Cold Spring Harbor Laboratory, New York).

cDNA sequence analysis

Sequencing was done in M13mpl8 DNA in both orientations by the Dideoxy chain termination method using Sequenase Version 2.0 (United States Biochemical Corporation). To read the complete cDNA sequence, deletions were generated in both orientations using Exonuclease III and S1 nuclease (Sambrook J., Fritsch, E. F. & Maniatis, T., supra. Orientation of the insert in the lambda gt 11 clone was directly determined in lambda gt11 by using lambda gt11 primers in sequencing.

Northern blot analysis

Total cellular RNA (10 $\mu$g) was denatured with glyoxal and separated by electrophoresis on 2% agarose gel containing glyoxal. The amount of RNA and the integrity of rRNA was confirmed by ethidium bromide staining of a duplicate gel. Gel was blotted onto Gene Screen plus membrane (DuPont) and probed with AmA1 cDNA labeled to a specific activity of about $3\times10^8$ cpm/$\mu$g DNA (Feinberg, A. & Vogelstein, B. (1984) *Anal. Biochem.* 137, 266–267).

PCR Aided Genomic cloning

Genomic DNA was isolated from seeds by the procedure of Rogers & Bendich (In Plant Mol. Biol. Manual, eds: Gelvin SB & Schilperoort RA, Kluwer Academic Publishers).

The genomic DNA was amplified to get the genomic clone of AmA1 by polymerase chain reaction using one forward primer and another reverse primer.

The forward primer was designed and made such that after amplification the amplified fragment will have the starting ATG. PCR was done in a 25 $\mu$l reaction volume using 350 ng of genomic DNA as template with Taq DNA polymerase by Perkin Elmer Cetus and components from GeneAmp® kit. The amplification was done in a PTC-100 - 60 thermal cycler of M. J.Res. Inc., (USA). The reaction mixture was made according to manufacturer instruction. This PCR amplified Genomic fragment was then cloned in pBluescript ks$^+$ at EcoRV site by the procedure of Marchuk D. (Nucleic Acid Research, 5: 1154, 1991).

Results

Figure 3A:
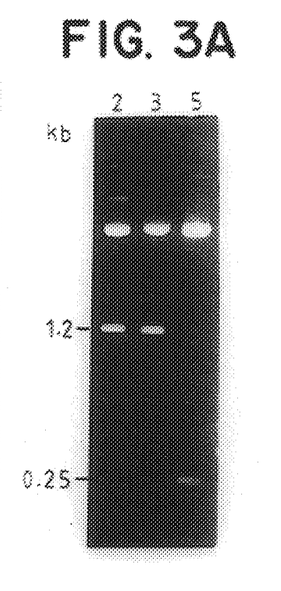
(FIG. 3A) Inserts from lambda clones 2, 3, and 5, were subcloned in pTZ18U vector. All three clones were digested with EcoRI and analysed on a 2% agarose gel. Clone numbers are shown above the lanes.
Figure 3B:
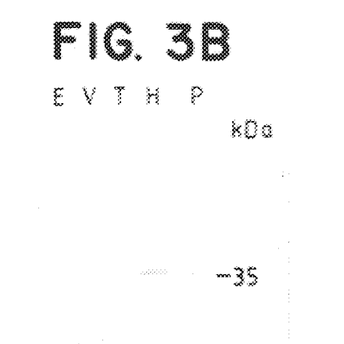
(FIG. 3B) Hybrid-selected translation product of subclone 3 was immunoprecipitated with AmA1 antibodies bound to protein A-Sepharose and analyzed by SDS/PAGE on a 12% gel. The $^{35}$S labeled and immunoprecipitated 35 kDa protein was detected by autoradiography.

Molecular Cloning of AmA1 cDNA:

cDNA clones corresponding to AmA1 were isolated from a cDNA library constructed in an expression vector lambda gt11. Level of AmA1 mRNA in developing seeds was analysed by in vitro translation and immunoprecipitation. Poly (A)+ RNA, from the stages when the level of AmA1 mRNA was high, was used as the template for cDNA synthesis. A total of 35,000 plaques were obtained of which six were immunopositive. Positive plaques were selected and subjected to successive rounds of phage titering and screening to get clonally pure recombinant plaques. DNA was isolated and Southern hybridization was done to see the relatedness of all the clones. Three of the clones designated AmA1.2, AmA1.3 and AmA1.5 were subcloned in plasmid vector pTZ18U. pAmA1.2 and pAmA1.3 had large inserts of 1.2 kb each and pAmA1.5 had an insert of 0.25 kb (FIG. 3A). pAmA1.3 was used for hybrid selected translation. Translated product when immunoprecipitated and analysed on SDS/PAGE gave a polypeptide of 35 kDa that comigrated with the 35 kDa band of purified AmA1 (FIG. 3B). This band was absent when no exogenous RNA was present in the translation reaction or when vector alone was used for hybridization.

Figure 4A:
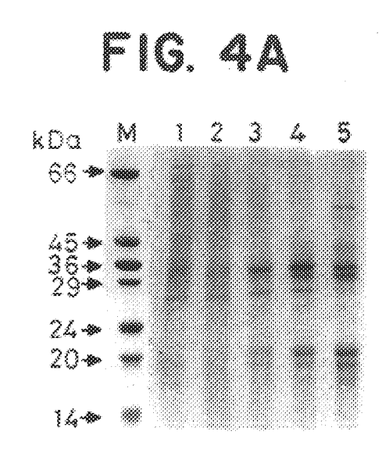
Figure 4B:
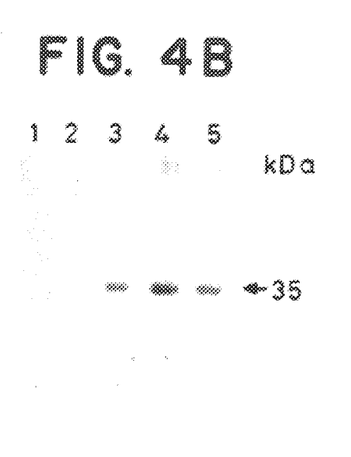
Figure 4C:
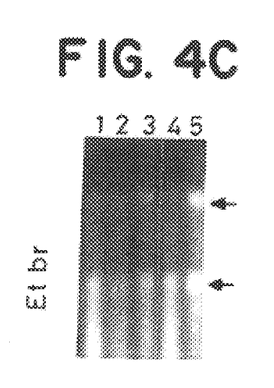
Figure 4D:
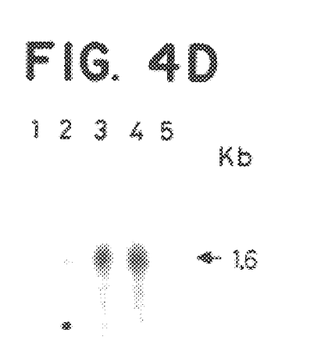
Figure 5A:
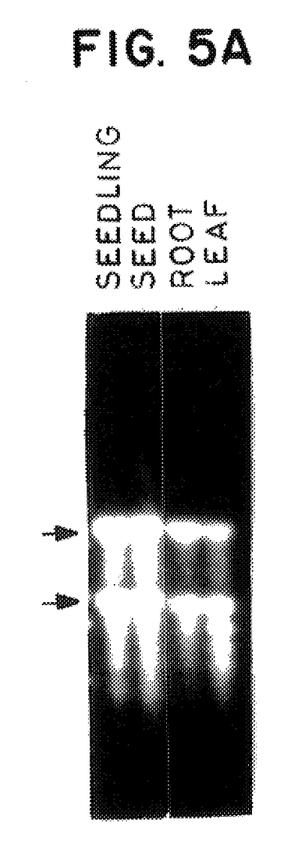
Figure 5B:
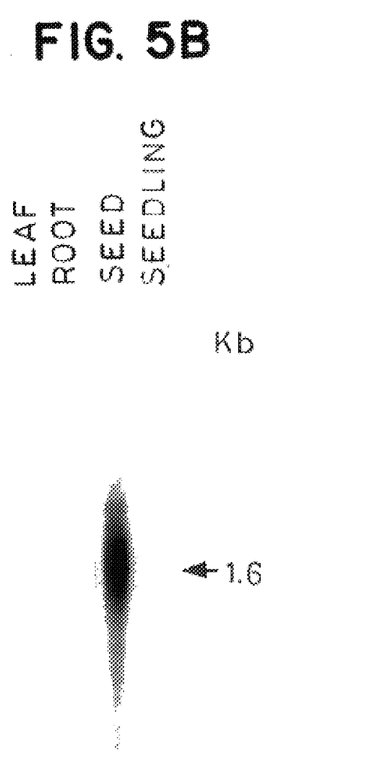

Developmental regulation and seed specific expression of AmA1:

Expression of most seed protein genes is regulated in time and in space. To study the developmentally regulated expression of AmA1 gene, total protein and RNA from seeds at different developmental stages were analysed. Seeds of Amaranthus appear in glomerules. At a particular time point in each glomerule seeds at various developmental stages are encountered. Seeds were therefore grouped into developmental stages by their weight (Table I). AmA1, as analysed by SDS/PAGE and Western blot analysis was seen to be synthesized very early on embryogenesis (FIGS. 4A & 4B). Total RNA when subjected to Northern blot analysis also showed the presence of AmA1 mRNA during early embryogenesis (FIGS. 4C & 4D). Mature seeds showed low levels of AmA1 RNA and no RNA was detected in one day old seedlings. Protein level was seen to increase in proportion to the RNA level until stage IV (Table I, FIGS. 4A–4D) after which there was no further increase in protein in spite of the presence of AmA1 mRNA. AmA1 was not detected in other plant parts (data not shown). Northern blot analysis did not show any trace of AmA1 mRNA either in leaves or in roots (FIG. 5). Therefore, these results suggest that the expression of AmA1 is seed specific.

TABLE I

Average weight of seeds at different stages of development

| STAGE | SEED WEIGHT (in mg) |
| --- | --- |
| I | 0.1 |
| II | 0.2 |
| III | 0.3 |
| IV | 0.4 |
| V (Mature) | 0.8 |

Sequence analysis of AmA1 cDNA

Figure 6:
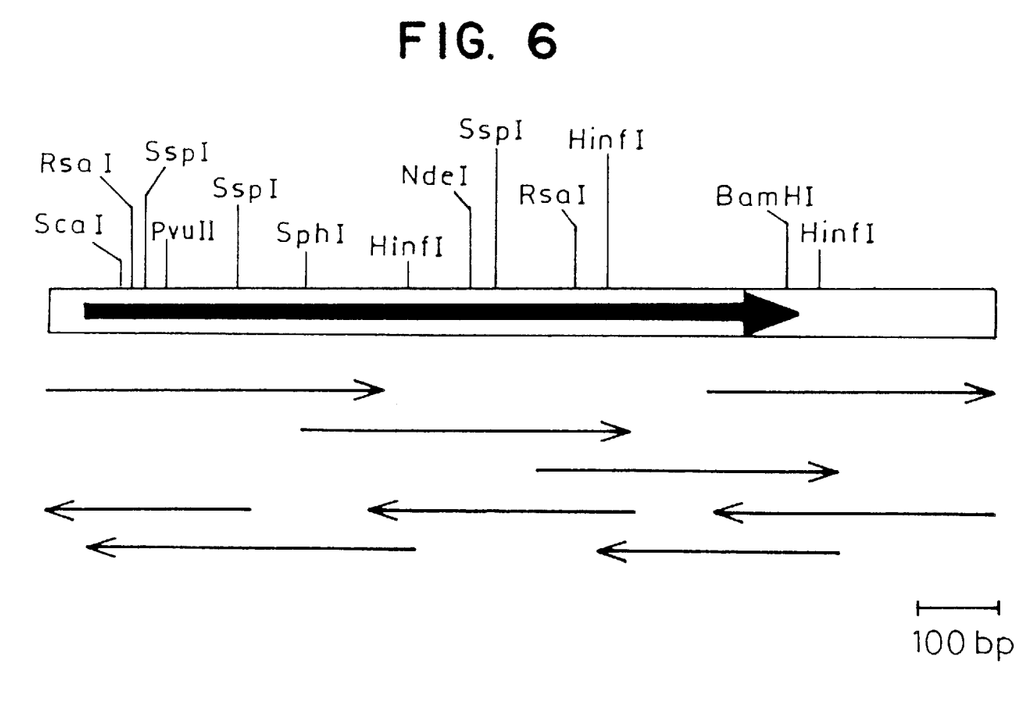
FIG. 6 - Sequencing strategy and the restriction map of AmA1 cDNA. The direction of transcription and length of the open reading frame is indicated by the solid thick arrow. The short thin horizontal arrows indicate the sequencing strategy used in both orientations.

The largest insert of 1.2 kb (from pAmA1.3) was subcloned in M13mp18 in both orientations to get single stranded DNA. The sequencing strategy is summarized in FIG. 6. The sequenced cDNA (FIG. 7A) has a length of 1183 base pairs with an open reading frame (ORF) of 912 bp with non-coding 5' and 3' flanking sequences. The ORF encodes a protein of 304 amino acids with Mr of 35000 and pH of 6.8. Analysis of the amino acid sequence shows that it is a hydrophilic protein with a small stretch of hydrophobic amino acids at the N-terminus (FIG. 7B). Amino acid composition as predicted from the cDNA sequence shows high levels of essential amino acids. It is similar to the composition obtained by protein hydrolysis (Table II). The differences observed are due to technical limitations with Picotag system of amino acid analysis as it normally shows reduced levels of sulphur amino acids and high levels of glycine. Poly A stretch is missing from the sequence though two putative poly-adenylation signals are located at 50 and 194 bp downstream of the stop codon (FIG. 7A). No homology was seen between the deduced protein sequence of AmA1 cDNA and other seed specific proteins.

TABLE II amino acid composition of Ama1

| Amino acid | Residues, mol % | |
| --- | --- | --- |
| | Purified Protein | cDNA sequence |
| Phe | 5.6. | 5.6 |
| Tyr | 4.8 | 4.9 |
| Leu | 7.6 | 8.6 |
| Ile | 5.0 | 6.6 |
| Val | 5.6 | 6.2 |
| Met | 1.6 | 2.3 |
| Cys | 0.7 | 1.6 |
| Ala | 5.3 | 4.6 |
| His | 3.3 | 2.3 |
| Thr | 5.3 | 5.9 |
| Pro | 3.6 | 3.6 |
| Gly | 12.0 | 5.3 |
| Glx | 8.9 | 9.2 |
| Asx | 16.6 | 14.5 |
| Ser | 6.6 | 6.9 |
| Arg | 5.3 | 2.6 |
| Lys | 6.6 | 6.9 |
| Trp | * | 2.3 |

*not determined

The amino acid composition as obtained from purified protein and also what is predicted from the cDNA sequence shows a high proportion of essential amino acids like lys, leu, thr, phe, val and sulfur amino acids (Table III) that are otherwise deficient in the major seed proteins of legumes and cereals. It has a relatively low level of glutamine as compared to other seed storage proteins (Higgins, T. J. V. (1984) Annu. Rev. Plant Physiol. 35, 191–221). Interestingly, AmA1 composition closely matches the values recommended by WHO making it more important nutritionally.

TABLE III

Percentage of essential amino acids of AmA1 in comparison to the World Health Organization recommended values.

| | % of total amino acids | | |
| --- | --- | --- | --- |
| Amino acids Total Protein | Amaranth Proceedings of the Second Amaranth Conference [Senft, J. P (1980). Rodale, Emmaus, PA; pp. 43–47] | AmA1 Calculated by considering total residue number of each amino acid from the sequence and their respective molecular weights. | WHO Proceedings of the Second Amaranth Conference [Senft, J. P (1980) Rodale, Emmaus, PA; pp. 43–47] |
| Trp | 1.4 | 3.6 | 1.0 |
| Met/Cys | 4.4 | 3.9 | 3.5 |
| Thr | 2.9 | 5.1 | 4.0 |
| Ile | 3.0 | 6.1 | 4.0 |
| Val | 3.6 | 5.2 | 5.0 |

TABLE III-continued

Percentage of essential amino acids of AmA1 in comparison to the World Health Organization recommended values.

| Amino acids Total Protein | Amaranth Proceedings of the Second Amaranth Conference [Senft, J. P (1980). Rodale, Emmaus, PA; pp. 43–47] | AmA1 Calculated by considering total residue number of each amino acid from the sequence and their respective molecular weights. | WHO Proceedings of the Second Amaranth Conference [Senft, J. P (1980) Rodale, Emmaus, PA; pp. 43–47] |
|---|---|---|---|
| Lys | 5.0 | 7.5 | 5.5 |
| Phe/Tyr | 6.4 | 13.7 | 6.0 |
| Leu | 4.7 | 9.2 | 7.0 |

WHO, World Health Organization.

Molecular cloning and sequence analysis of PCR amplified genomic clone

Figure 8:
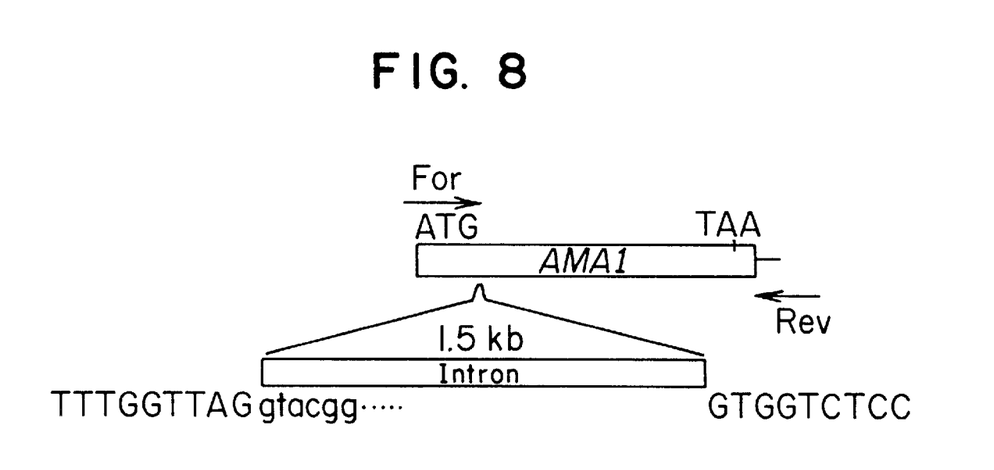
FIG. 8 - Position of intron in genomic clone of AmA1. The forward primer and the reverse primer were positioned and shown by arrow heads. The junction of the intron start and end sites were shown by the sequences mentioned.
Figure 9A:
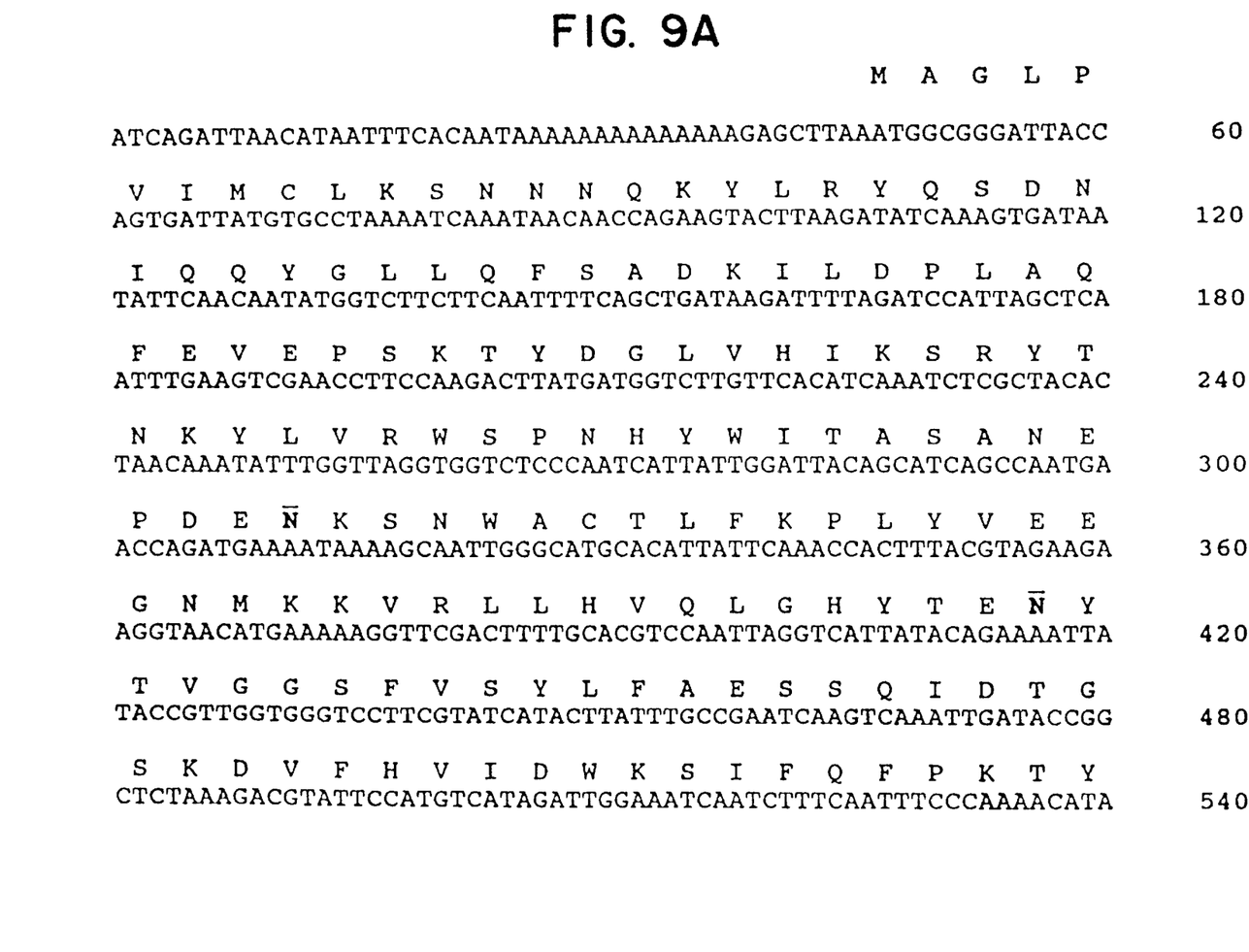
FIGS. 9A and 9B - Nucleotide sequence of the 1183-bp AmA1 cDNA and the derived amino acid sequence of the predicted polypeptide. Amino acids (single-letter code) are indicated above the first base of each codon. Possible glycolation sites are overlined. It does not show poly (A) tract although poly (A) addition signals are indicated and are underlined.
Figure 9B:
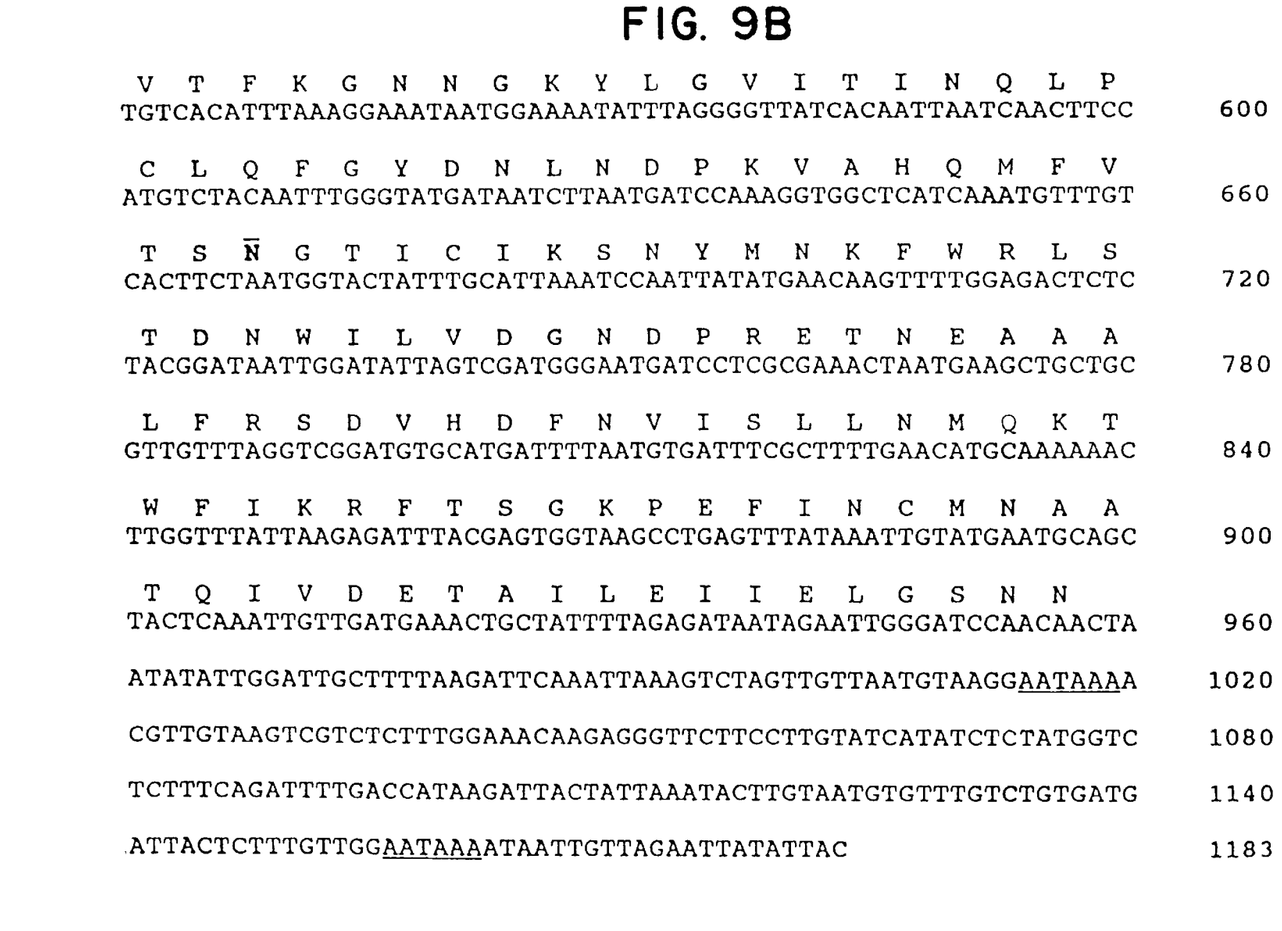

The PCR amplified genomic clones were picked up by colony hybridization using Duralon UV membrane according to manufacturer instruction with AmA1 cDNA as probe. The positive clones were having 2.5 kb insert comprises of the open reading frame interrupted by an intron approximately 1.5 kb in length and some part of poly(A) tail (FIG. 8). The intron is being sequenced by the dideoxy chain termination method using Vent DNA polymerase and components from CircumVent™ Thermal Cycle Sequencing Kit (New England Biolabs, USA). To read the complete sequence, deletions were generated using exonuclease III and S1 nuclease (Sambrook, J., Fritsch, E. F. & Maniatis, T., supra.

Figure 7:
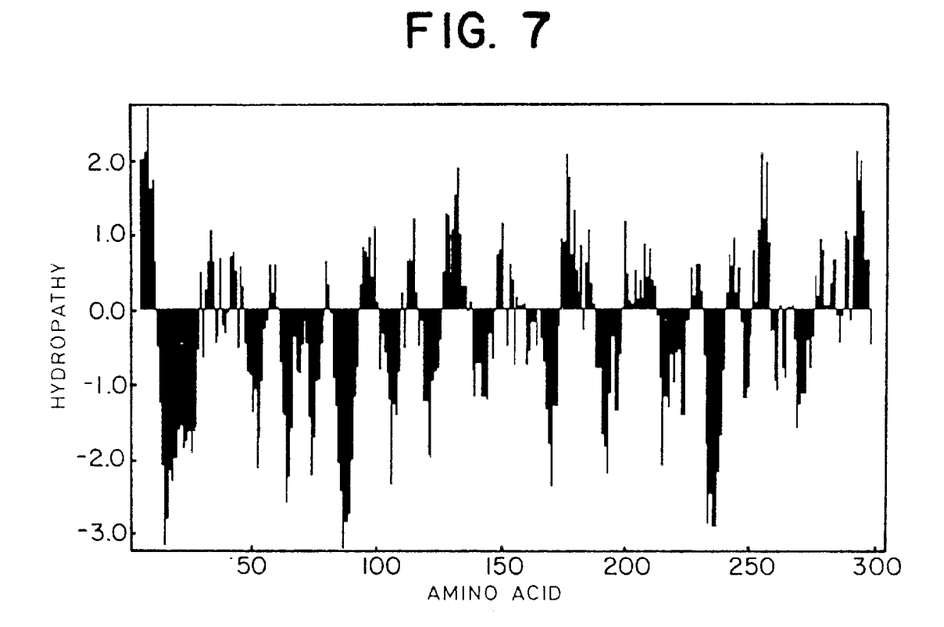
FIG. 7 - Hydropathic plot of the AmA1 protein. The 304-amino acid sequence of the predicted AmA1 protein was analyzed by the method of Kyte and Doolittle with a window setting of 7.

Seed storage proteins are localized within protein bodies and are often glycosylated. AmA1 was found to be present in the cytosol and not localized within protein bodies. This was confirmed by cDNA analysis. The putative polypeptide encoded by the ORF of AmA1 cDNA is 35 kDa. In addition, AmA1 mRNA on hybrid selected translation gave a polypeptide of 35 kDa that matched the size of the purified protein (FIG. 3B). Hydropathy plot of the deduced protein sequence indicates the presence of a small stretch of hydrophobic amino acids near the N-terminus (FIG. 7). Any possible functional relevance for this region is not yet established. This does not appear to be a signal peptide as the amino acids following this stretch do not meet the requirement of a signal sequence (Perlman, D. & Halvorsen, H. O. (1977) *J. Mol. Biol.* 115, 675–694 and Von Heijne, G. (1984) *J. Mol. Biol.* 173, 243–251). Three putative glycosylation sites are also present in the sequence though the protein did not show any glycosylation by PAS staining (data not shown). AmA1 gene is expressed during early embryogenesis. Mature seeds even after one year of storage showed the presence of AmA1 mRNA, though the level was reduced. It suggests that it is very stable. Germinated seeds did not show any AmA1 mRNA. No RNA was detected in leaves and roots, suggesting that the expression is tissue specific. Such specificity of expression is due to sequences in the promoter and enhancer regions of the gene that we are now looking into.

To summarize, it can be said that AmA1 is a seed specific protein, different from the traditional seed storage proteins. Because of its high nutritional value gene encoding this protein may have potential for compensating for amino acid deficiencies of many seed proteins once it is genetically engineered into target plants.

---

† SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1183 base pairs
        ( B ) TYPE: Nucleic acid
        ( C ) STRANDEDNESS: Single
        ( D ) TOPOLOGY: Linear     ( i i ) MOLECULE TYPE: cDNA     ( x i ) SEQUENCE DESCRIPTION: SEQ ID NO:1:

```
    ATCAGA   TTAACATAAT   TTCACAATAA   AAAAAAAAAA   AAGAGCTTAA                    46

ATG  GCG  GGA  TTA  CCA  GTG  ATT  ATG  TGC  CTA  AAA  TCA  AAT  AAC            88
Met  Ala  Gly  Leu  Pro  Val  Ile  Met  Cys  Leu  Lys  Ser  Asn  Asn
 1                    5                        10

AAC  CAG  AAG  TAC  TTA  AGA  TAT  CAA  AGT  GAT  AAT  ATT  CAA  CAA           130
Asn  Gln  Lys  Tyr  Leu  Arg  Tyr  Gln  Ser  Asp  Asn  Ile  Gln  Gln
 15                   20                       25

TAT  GGT  CTT  CTT  CAA  TTT  TCA  GCT  GAT  AAG  ATT  TTA  GAT  CCA           172
Tyr  Gly  Leu  Leu  Gln  Phe  Ser  Ala  Asp  Lys  Ile  Leu  Asp  Pro
           30                  35                       40

TTA  GCT  CAA  TTT  GAA  GTC  GAA  CCT  TCC  AAG  ACT  TAT  GAT  GGT           214
Leu  Ala  Gln  Phe  Glu  Val  Glu  Pro  Ser  Lys  Thr  Tyr  Asp  Gly
```

```
                      45                         50                             55
CTT  GTT  CAC  ATC  AAA  TCT  CGC  TAC  ACT  AAC  AAA  TAT  TTG  GTT         256
Leu  Val  His  Ile  Lys  Ser  Arg  Tyr  Thr  Asn  Lys  Tyr  Leu  Val
               60                    65                            70

AGG  TGG  TCT  CCC  AAT  CAT  TAT  TGG  ATT  ACA  GCA  TCA  GCC  AAT         298
Arg  Trp  Ser  Pro  Asn  His  Tyr  Trp  Ile  Thr  Ala  Ser  Ala  Asn
                    75                         80

GAA  CCA  GAT  GAA  AAT  AAA  AGC  AAT  TGG  GCA  TGC  ACA  TTA  TTC         340
Glu  Pro  Asp  Glu  Asn  Lys  Ser  Asn  Trp  Ala  Cys  Thr  Leu  Phe
 85                         90                          95

AAA  CCA  CTT  TAC  GTA  GAA  GAA  GGT  AAC  ATG  AAA  AAG  GTT  CGA         382
Lys  Pro  Leu  Tyr  Val  Glu  Glu  Gly  Asn  Met  Lys  Lys  Val  Arg
      100                        105                      110

CTT  TTG  CAC  GTC  CAA  TTA  GGT  CAT  TAT  ACA  GAA  AAT  TAT  ACC         424
Leu  Leu  His  Val  Gln  Leu  Gly  His  Tyr  Thr  Glu  Asn  Tyr  Thr
           115                       120                      125

GTT  GGT  GGG  TCC  TTC  GTA  TCA  TAC  TTA  TTT  GCC  GAA  TCA  AGT         466
Val  Gly  Gly  Ser  Phe  Val  Ser  Tyr  Leu  Phe  Ala  Glu  Ser  Ser
               130                       135                     140

CAA  ATT  GAT  ACC  GGC  TCT  AAA  GAC  GTA  TTC  CAT  GTC  ATA  GAT         508
Gln  Ile  Asp  Thr  Gly  Ser  Lys  Asp  Val  Phe  His  Val  Ile  Asp
                    145                        150

TGG  AAA  TCA  ATC  TTT  CAA  TTT  CCC  AAA  ACA  TAT  GTC  ACA  TTT         550
Trp  Lys  Ser  Ile  Phe  Gln  Phe  Pro  Lys  Thr  Tyr  Val  Thr  Phe
155                           160                       165

AAA  GGA  AAT  AAT  GGA  AAA  TAT  TTA  GGG  GTT  ATC  ACA  ATT  AAT         592
Lys  Gly  Asn  Asn  Gly  Lys  Tyr  Leu  Gly  Val  Ile  Thr  Ile  Asn
      170                        175                      180

CAA  CTT  CCA  TGT  CTA  CAA  TTT  GGG  TAT  GAT  AAT  CTT  AAT  GAT         634
Gln  Leu  Pro  Cys  Leu  Gln  Phe  Gly  Tyr  Asp  Asn  Leu  Asn  Asp
           185                       190                      195

CCA  AAG  GTG  GCT  CAT  CAA  ATG  TTT  GTC  ACT  TCT  AAT  GGT  ACT         676
Pro  Lys  Val  Ala  His  Gln  Met  Phe  Val  Thr  Ser  Asn  Gly  Thr
                200                       205                     210

ATT  TGC  ATT  AAA  TCC  AAT  TAT  ATG  AAC  AAG  TTT  TGG  AGA  CTC         718
Ile  Cys  Ile  Lys  Ser  Asn  Tyr  Met  Asn  Lys  Phe  Trp  Arg  Leu
                    215                       220

TCT  ACG  GAT  AAT  TGG  ATA  TTA  GTC  GAT  GGG  AAT  GAT  CCT  CGC         760
Ser  Thr  Asp  Asn  Trp  Ile  Leu  Val  Asp  Gly  Asn  Asp  Pro  Arg
225                           230                       235

GAA  ACT  AAT  GAA  GCT  GCT  GCG  TTG  TTT  AGG  TCG  GAT  GTG  CAT         802
Glu  Thr  Asn  Glu  Ala  Ala  Ala  Leu  Phe  Arg  Ser  Asp  Val  His
      240                        245                      250

GAT  TTT  AAT  GTG  ATT  TCG  CTT  TTG  AAC  ATG  CAA  AAA  ACT  TGG         844
Asp  Phe  Asn  Val  Ile  Ser  Leu  Leu  Asn  Met  Gln  Lys  Thr  Trp
           255                       260                      265

TTT  ATT  AAG  AGA  TTT  ACG  AGT  GGT  AAG  CCT  GAG  TTT  ATA  AAT         886
Phe  Ile  Lys  Arg  Phe  Thr  Ser  Gly  Lys  Pro  Glu  Phe  Ile  Asn
                270                       275                     280

TGT  ATG  AAT  GCA  GCT  ACT  CAA  ATT  GTT  GAT  GAA  ACT  GCT  ATT         928
Cys  Met  Asn  Ala  Ala  Thr  Gln  Ile  Val  Asp  Glu  Thr  Ala  Ile
                    285                       290

TTA  GAG  ATA  ATA  GAA  TTG  GGA  TCC  AAC  AAC  TAATATATTG  GATT         972
Leu  Glu  Ile  Ile  Glu  Leu  Gly  Ser  Asn  Asn
295                           300

GCTTTTAAGA  TTCAAATTAA  AGTCTAGTTG  TTAATGTAAG  GAATAAAACG              1022

TTGTAAGTCG  TCTCTTTGGA  AACAAGAGGG  TTCTTCCTTG  TATCATATCT              1072

CTATGGTCTC  TTTCAGATTT  TGACCATAAG  ATTACTATTA  AATACTTGTA              1122
```

-continued

| | | | | | |
|---|---|---|---|---|---|
| ATGTGTTTGT | CTGTGATGAT | TACTCTTTGT | TGGAATAAAA | TAATTGTTAG | 1172 |
| AATTATATTA | C | | | | 1183 |

We claim:

1. A substantially pure AmA1 protein.
2. The AmA1 according to claim 1 wherein said AmA1 is encoded in the DNA sequence of SEQ ID NO: 1.
3. A composition comprising a substantially pure AmA1 protein and an nutritionally acceptable carrier.

* * * * *

UNITED STATES PATENT AND TRADEMARK OFFICE
CERTIFICATE OF CORRECTION

PATENT NO : 5,849,352
DATED : December 15, 1998
INVENTOR(S) : Asis DATTA, et al.

It is certified that error appears in the above-identified patent and that said Letters Patent are hereby corrected as shown below:

On the title page, under Inventors, line 2, delete "Nevru" and insert --Nehru--.

Signed and Sealed this

Fifteenth Day of May, 2001

Attest:

NICHOLAS P. GODICI

Attesting Officer

Acting Director of the United States Patent and Trademark Office